United States Patent [19]

Ashmead

[11] 4,169,716

[45] Oct. 2, 1979

[54] SYNERGISTIC METAL PROTEINATE PLANT HORMONE COMPOSITIONS

[76] Inventor: Harvey H. Ashmead, 719 E. Center St., Kaysville, Utah 84037

[21] Appl. No.: 885,539

[22] Filed: Mar. 13, 1978

[51] Int. Cl.$^2$ .................. A01N 21/02; A01N 9/24; A01N 9/12; A01N 9/22

[52] U.S. Cl. .................................... 71/77; 71/89; 71/92; 71/97; 71/79; 71/114; 71/117; 71/118; 71/120; 71/122; 71/127

[58] Field of Search .................. 71/89, 77, 122, 92, 71/79, 97

[56] References Cited

U.S. PATENT DOCUMENTS

| | | | |
|---|---|---|---|
| 2,802,306 | 8/1957 | Leopold et al. | 71/77 |
| 2,903,455 | 9/1959 | Strong et al. | 71/77 |
| 2,966,488 | 12/1960 | Shive et al. | 71/77 |
| 2,993,048 | 7/1961 | Shive et al. | 71/89 |
| 3,118,753 | 1/1964 | Shive et al. | 71/77 |
| 3,738,822 | 6/1973 | Asahi et al. | 71/89 |
| 3,873,296 | 3/1975 | Ashmead et al. | 71/77 |

FOREIGN PATENT DOCUMENTS

| | | | |
|---|---|---|---|
| 634472 | 1/1962 | Canada | 71/89 |
| 1270879 | 7/1961 | France | 71/77 |
| 513651 | 2/1976 | Japan | 71/89 |
| 7505401 | 11/1975 | Netherlands | 71/89 |

OTHER PUBLICATIONS

Ries et al., "Triacontavol; A New Naturally Occurring, etc.," (1977). CA86, No. 184463h, (1977).
Ries et al., "Growth Responses of Rice Seedlings, etc.," CA87, No. 96745s, (1977).

*Primary Examiner*—Glennon H. Hollrah
*Attorney, Agent, or Firm*—Criddle, Thorpe & Western

[57] ABSTRACT

A combination of metal proteinates with triacontanol and one or more plant hormones selected from the group consisting of auxins, cytokinins, brassins, kinins, and gibberellins form synergistic compositions wherein plant growth is stimulated and the absorption of essential metals is significantly increased.

10 Claims, No Drawings

4,169,716

SYNERGISTIC METAL PROTEINATE PLANT HORMONE COMPOSITIONS

BACKGROUND OF THE INVENTION

This invention relates to a synergistic composition of plant growth nutrients and regulators. More specifically this invention relates to a novel combination of plant nutrients and regulators which are, in themselves, known to be beneficial to plant growth and regulation but which, in combination, show a significantly greater effect than when used separately, i.e. a synergistic effect.

It is known that metal proteinates, which are chelates of bio-essential metals with protein hydrolysate ligands, increase metal assimilation in plants as shown in U.S. Pat. No. 3,893,269. It is also known that triacontanol, which is a straight chained thirty carbon saturated alcohol having the formula $CH_3(CH_2)_{28}CH_2OH$, has plant growth characteristics. See, for example, Ries, et al., Science Mar. 25, 1977, Vol. 195 pp. 1339-1341. It has long been known that there are various plant growth hormones consisting of auxins, cytokinins, brassins and gibberellins. Cytokinins are obtained as extracts from seaweed and zeatin. Cytokinins may be regarded as derivatives of adenine, a purine compound. The biological effects of cytokinins are stated to be cell division, preservation of chlorophyll, expansion of young leaves, formation of new shoots or roots, outgrowth of lateral buds, promotion of seed germination and breaking of dormancy.

Auxins which include indoleacetic acid and derivatives thereof and gibberellins which include gibberellic acid and its derivatives increase fruit set and stimulate the sprouting of buds. These hormones are usually obtained from seaweed extracts and rice respectively.

The brassins are obtained from rape pollen and are a group of unidentified compounds that induce elongation of plants. It is thought that these compounds have a glyceride structure.

The presently known essential polyvalent metals in plant nutrition and biological development are calcium, magnesium, zinc, iron, manganese, copper, cobalt, molybdenum and boron. There is also evidence that other elements, such as selenium may have significant, direct or indirect, influence on biological activity.

Metals are believed to be mobilized in biological tissues through the formation of metal chelates, and if the metabolism of the organism does not readily facilitate chelate formation, metal assimilation and transport will be inhibited. Metal chelates which are also referred to as metal proteinates as will be hereinafter described are superior to inorganic metal compounds in facilitating metal absorption and transport because many plants have an inherent defect which inhibits natural endogenic synthesis of metal chelates.

The term "chelate" is stated in Webster's Seventh New Collegiate Dictionary, 1965, as being derived from the Greek chele meaning "claw" and is defined as "of relating to, or having a cyclic structure usually containing five or six atoms in a ring in which a central metallic ion is held in a coordination complex." A chelate has no net electrical charge on the central metal ion.

In connection with the above definition, metal chelates are herein defined to mean an essential metal atom attached by more than one donor atom of a ligand in such a manner as to form a heterocyclic ring by coordination complex bonding. By coordinate complex bonding is meant both covalent and ionic bonding. The term ligand refers to atoms, ions or molecules of hydrolyzed protein which are capable of functioning as the donor partner in one or more coordinate bonds. In other words, the ligand is electron rich and/or proton deficient. Ligands having two or more atoms which can simultaneously serve as donors are sometimes called polydentate ligands. Polydentate ligands whose structures permit the attachment of two or more donor sites to the same metal ion simultaneously, thus closing one or more heterocyclic rings, are called chelate ligands. In this specification, the terms chelate ligand and ligand will be used interchangeably and will preferably be referred to as ligand.

From the above it is apparent that a ligand must have available electrons in order to react with the metal ion to form a coordination complex or chelate. Obviously, the more acidic a solution is the more protons will interfere or compete for electrons and the less readily a chelate will form. Therefore, in the case of protein hydrolysates, i.e. polypeptides, peptides and naturally occurring amino acids the alpha amino groups ($-NH_2$) should be free from interfering protons ($NH_3^{\oplus}$) and the carboxylic acid groups should have the protons removed to from carboxy ($-COO^{\ominus}$) groups. This is a situation which occurs when the pH is more basic than the isoelectric point of the particular molecule in question. While each molecule has its own isoelectric point or zwitter ionic state it is not possible to have a stated isoelectric point for a group of different molecules such as protein hydrolysates, and thus the terms must be described more functionally, i.e., the mixture must be sufficiently basic that interfering protons are removed from the protein hydrolysate ligand.

1-triacontanol (1-hydroxytriacontane) is a naturally occurring straight chain 30 carbon saturated aliphatic alcohol present in beeswax and the leaves of many plants, particularly alfalfa. Triacontanol is unique in its activity as compared to homologs thereof. Saturated fatty alcohols with chain lengths of 9, 10 and 11 carbon atoms are active inhibitors of apillary and terminal bud growth. Alcohols with 17 to 22 carbons and their esters show some growth activity. However, octocosanol, the 28 carbon homolog of triacontanol, applied in nutrient culture at the same concentration as triacontanol does not increase plant growth or water uptake.

Triacontanol, applied in nutrient culture solution to rice seedlings in minute quantities, caused an increase in dry weight and leaf areas of plants, such as corn, wheat, rice, soybeans, tomatoes, carrots, cucumbers, lettuce and other food plants.

OBJECT OF THE INVENTION

It is an object of this invention to provide a novel composition of matter.

It is another object of this invention to provide a synergistic composition of matter which has a greater effect on the development of plants than the components of the composition when used separately.

A primary object of the present invention is to provide a novel combination of compounds to form a composition of matter, which composition is significantly more effective in making essential metals available to plant tissues and increasing plant growth, regardless of the endogenic synthesizing capability of the plants, than individual compounds of the composition administered separately.

These and other objects will become more fully apparent from the following description and appended claims.

DESCRIPTION OF THE INVENTION

It has been found that a mixture of one or more metal proteinates with triacontanol and one or more plant hormones selected from the group consisting of auxins, kinins, cytokinins, gibberellins and brassins produce a synergistic effect on plant growth and development and mineral uptake and translocation.

Preferably the mixture of metal proteinates, triacontanol and hormones is applied as an aqueous foliar spray maintained at a pH of about 7 to 8 by buffering. Other methods of application include seed treatment, side dressing or banding of the soil and and by the regulated application of the compositions to irrigation water.

The mixture of metal proteinates, triacontanol and other plant hormones shall hereinafter be referred to as a "composition".

Compositions are prepared by dissolving the compounds in water to form a concentrate having the desired concentration. Surfactants, wetting agents or other additives may also be added if desired. The concentration will depend somewhat upon the solubility of compounds in the composition. The concentrate is preferably diluted with an amount of water necessary to supply the desired amount of composition to the plants. Rather than forming a concentrate the composition can be added directly to water in a spray tank or other container and dissolved to form a solution that is suitable for direct application.

Since the concentration of metals that are essential for plant nutrition and development will vary according to each metal it is impossible to state with accuracy what the metal proteinate content in a given composition will be. Generally speaking metal proteinates are usually applied so as to provide from 0.45 to 900 grams per acre of each metal in the form of a metal proteinate. Thus if two or more metals are simultaneously applied the metal proteinate concentration will increase. Since the metal requirements of plants will vary according to the plant and the metal used the concentration used will be referred to as an "effective amount". Effective amounts can be calculated or empirically determined by one having ordinary skill in the art.

Triacontanol is effective when applied in relatively minute amounts. The application rate will generally vary from about $1 \times 10^{-6}$ to 2 grams per acre. Again the concentration in the solution being applied will depend upon concentrations of other components in the composition. However, the term "effective amount" will refer to a concentration sufficient to provide the above given doseages per acre.

Similarly with other hormones such as auxins, cytokinins, kinins, gibberellins and brassins, the term "effective amount" will vary according to the hormone used. Generally each hormone will be present in solution in such a concentration to provide $1 \times 10^{-5}$ to 4.0 grams per acre with 0.001 to 2 grams being preferred.

If side dressing or banding is used the composition may ba applied as a solid in powder or granulated form. The composition will preferably contain metal proteinates wherein each metal is present in an amount ranging from 0.45 to 900 parts by weight as a metal proteinate, triacontanol which is present in amounts ranging from $1 \times 10^{-6}$ to 2 parts by weight with the remaining hormones being present in amounts ranging from $1 \times 10^{-5}$ to 4 parts by weight.

The invention does not lie so much in concentrations as in the discovery that the components comprising the composition will provide a synergistic effect when used together.

The invention can best be illustrated by the following data taken from an extensive examination of controls, inorganic fertilizers, metal proteinates used alone and combined with triacontanol and other plant hormones. This illustration is for purposes of showing the superiority of the present invention but is not intended in any to be self limiting as to the scope of the invention.

EXAMPLE I

One gallon each of the following solutions were made up and labeled in the following manner:

C. Control solution of water

W. Inorganic fertilizer solution containing 2 grams of the following formula dissolved in 1 gallon of water and buffered to a pH of about 7.4 with sodium carbonate
11.9% nitrogen
5.3% phosphorus ($P_2O_5$)
15.9% calcium ($Ca(NO_3)_2$)
1.3% magnesium ($MgSO_4$)
0.13% iron ($Fe_2(SO_4)_3$)
0.001% copper ($CuSO_4$)
0.02% manganese ($MnCl_2$)
1.8% sulfur
0.01% boron ($H_3B_3$)
0.03% chloride
0.0005% molybdenum ($MoO_3.H_2O$)

E. The exact same percent of nutrients as in solution W except the calcium, iron, copper, magnesium, manganese, zinc and molybdenum were added in the form of metal proteinates instead of the inorganic mineral of solution W.

F. The same solution as solution E having added thereto 0.4 mg of triacontanol per gallon.

G. The same solution as solution E having added thereto the plant hormones gibberellins, auxin and cytokinin at the rate of 50 PPM.

H. The same solution as solution G having added thereto triacontanol at the rate of 0.4 mg per gallon.

The solutions were tested in the following manner. Six portions consisting of 75 grams each of turkey red wheat were placed on the grid of six hydroponic trays identified as C, W, E, F, G and H respectively. Each grid was covered with absorbent cloth. 750 mls. of each of the above solutions were measured and placed in the corresponding identified tray. The wick from the grid within the tray dipped into the solution thereby carrying the solution to the grid and wetting all the seeds evenly. Additional water from each gallon container was added to the appropriately lettered tray corresponding to the identification on the gallon container to keep the solution level in each tray approximately even. No other source was used to water the wheat.

After 30 days the hydroponic experiment was terminated with the following results:

| | C | W | E | F | G | H |
|---|---|---|---|---|---|---|
| Height of wheat (inches) | 6.5 | 7.5 | 9 | 8 | 9 | 10.5 |
| Length of roots (inches) | 3 | 3 | 5 | 6 | 4.75 | 5.25 |
| Molding | bad | some | some | bad | some | very little |
| Weight at | | | | | | |

|  | -continued | | | | | |
|---|---|---|---|---|---|---|
|  | C | W | E | F | G | H |
| termination (grams) | 377 | 478 | 583 | 588 | 551 | 612 |

Percent increase of wheat in tray H in synergistic effect over the other trays in regards to height and weight is as follows:

| Tray | Height | Weight |
|---|---|---|
| C | 3.8 | 38.3 |
| W | 2.8 | 21.8 |
| E | 1.4 | 4.8 |
| F | 2.4 | 3.9 |
| G | 1.4 | 10.0 |

The leaves, roots and whole plant was assayed via atomic absorption spectrophotometry for comparative mineral uptake in the essential polyvalent metals iron, calcium, zinc, magnesium, manganese and copper. The wheat was also assayed for potassium, phosphorus and nitrogen content. The results obtained are shown in Table I and are reported in terms of milligrams of metal per gram of plant.

TABLE I

|  | Control | | | W | | | E | | |
|---|---|---|---|---|---|---|---|---|---|
|  | Leaves | Roots | Av. | Leaves | Roots | Av. | Leaves | Roots | Av. |
| Iron | .089 | 0.101 | .095 | .143 | .242 | .192 | .089 | .515 | .302 |
| Calcium | .347 | 0.327 | .337 | 3.219 | .189 | 1.704 | 3.570 | .626 | 2.068 |
| Zinc | .036 | 0.056 | .046 | .073 | .046 | .059 | .053 | .061 | .057 |
| Mg | 1.150 | 1.313 | 1.231 | 5.64 | 2.380 | 4.01 | 5.410 | 2.77 | 4.090 |
| Mn | 0.011 | 0.012 | 0.115 | .096 | .051 | .073 | .085 | .110 | .0975 |
| Cu | 0.047 | 0.051 | .049 | .0125 | .017 | .014 | .013 | .095 | .054 |
| K | 3.463 | 3.175 | 3.319 | 30.20 | 4.85 | 17.52 | 22.18 | 11.9 | 17.04 |
| P | 0.350 | .754 | .552 | 11.849 | 3.878 | 7.86 | 11.607 | 7.379 | 9.493 |
| N | 32.075 | 30.57 | 31.32 | 22.4 | 19.00 | 20.74 | 71.015 | 49.585 | 60.3 |

|  | Control F | | | G | | | H | | |
|---|---|---|---|---|---|---|---|---|---|
|  | Leaves | Roots | Av. | Leaves | Roots | Av. | Leaves | Roots | Av. |
| Iron | .127 | .586 | .356 | .104 | .269 | .186 | .103 | 1.049 | .576 |
| Calcium | .461 | .584 | .522 | 3.795 | 3.239 | 3.517 | .440 | 0.847 | .644 |
| Zinc | .066 | .056 | .061 | .074 | .053 | .063 | .060 | .074 | .067 |
| Mg | 5.71 | 2.43 | 4.07 | 7.07 | 2.12 | 4.59 | 6.390 | 4.49 | 5.44 |
| Mn | .120 | .092 | .106 | .115 | .072 | .0935 | .091 | .103 | .097 |
| Cu | .015 | .061 | .038 | .012 | .027 | .019 | .015 | .191 | .103 |
| K | 23.13 | 12.34 | 17.73 | 31.63 | 5.74 | 18.68 | 25.92 | 8.34 | 17.13 |
| P | 10.53 | 8.752 | 9.64 | 12.819 | 6.786 | 9.80 | 9.91 | 12.68 | 11.297 |
| N | 76.758 | 40.34 | 58.54 | 78.999 | 40.78 | 59.85 | 81.80 | 41.741 | 61.77 |

The composition of solution H produced significantly higher levels of minerals in virtually all cases as compared to the results obtained from the other solutions. The percent of synergistic increase of composition H over the other combinations is shown in Table II. In those tests where a synergistic effect was not shown the results are reported as (percent.) These effects were shown mostly in calcium and potassium. It should be noted that potassium is not polyvalent metal and no claim is made herein as to any increase of monovalent metals, i.e. alkali metals.

TABLE II

|  | Control | W | E | F | G |
|---|---|---|---|---|---|
| Iron | 83% | 66% | 45.8% | 38.1% | 67.7% |
| Ca | 47.6% | (6.2%) | (6.88%) | 1.89% | (81.6%) |
| ZN | 45% | 17% | 16.9% | 8.9% | 5.9% |
| Ma | 77.3% | 26.2% | 24.8% | 25.18% | 15.6% |
| MN | 88.8% | 26.2% | 2.02% | (6.6%) | 6.06% |
| Cu | 52.4% | 89% | 47.5% | 63.1% | 81.5% |
| K | 80.6% | (2.2%) | 5.2% | (3.38%) | (8.2%) |

TABLE II-continued

|  | Control | W | E | F | G |
|---|---|---|---|---|---|
| P | 95.1% | 93% | 15.9% | 14.6% | 13.2% |
| N | 49.2% | 66.4% | 2.3% | 5.2% | 3.10% |

EXAMPLE II

Comparative studies were conducted as in Example I using beans, corn, onions, carrots, tomatoes and parsnips in the place of wheat. The same lettering arrangement as used in Example I was followed for both solutions and trays. In all cases the composition containing the metal proteinates, triacontanol, and cytokinin, gibberellins and auxin (solution H) performed synergistically better. Charts and tables are not included but the average percent range of increase produced by solution H over the other solutions as regards weight, height and mineral uptake was determined.

| 1. | Average growth by weight | 5.3–4.1% |
|---|---|---|
| 2. | Average increase in plant height | 3.8–9.1% |
| 3. | Average increase in mineral uptake | 1.5–93.4% |

It is evident from the above examples that the combination of metal proteinates, triacontanol and at least one other plant hormone does indeed exhibit a synergistic effect on the growth, development and polyvalent metal uptake of plant tissues. As noted before, the results obtained in the above examples are illustrative only. The scope of this invention is to be limited only by the appended claims.

I claim:

1. A plant regulating composition consisting essentially of (1) an effective amount of an essential polyvalent metal selected from the group consisting of magnesium, zinc, iron, manganese, calcium, copper, cobalt, molybdenum, boron, and selenium and mixtures thereof wherein each metal present is in the form of a metal proteinate, (2) an effective amount of triacontanol and (3) an effective amount of a plant hormone selected from the group consisting of auxins, kinins, cytokinins, gibberellins and brassins and mixtures thereof wherein the weight ratio of each metal present in the form of a metal proteinate to triacontanol may vary from 0.225 to $9 \times 10^8$ and wherein the weight ratio of each plant hormone present to triacontanol may vary from $5 \times 10^{-6}$ to $4 \times 10^6$ in a biologically acceptable carrier.

2. A plant regulating composition according to claim 1 wherein the essential polyvalent metals are selected from the group consisting of magnesium, zinc, iron, manganese, calcium, copper and molybdenum.

3. A plant regulating biological composition according to claim 1 wherein the carrier is an aqueous solution buffered to a pH of between about 7 and 8.

4. A method for increasing plant growth and metal uptake in plants which comprises applying to such plants an effective amount of a plant regulating composition consisting of (1) an essential polyvalent metal selected from the group consisting of magnesium, zinc, iron, manganese, and selenium and mixtures thereof in the form of metal proteinates, (2) triacontanol and (3) one or more plant hormones selected from the group consisting of auxins, kinins, cytokinins, gibberellins and brassins and mixtures thereof wherein the weight ratio of each metal present in the form of a metal proteinate to triacontanol may vary from 0.225 to $9 \times 10^8$ and wherein the weight ratio of each plant hormone present to triacontanol may vary from $5 \times 10^{-6}$ to $4 \times 10^6$ in a biologically acceptable carrier.

5. A method according to claim 4 wherein each metal used in the form of a metal proteinate is applied at a rate of about 0.45 to 900 grams per acre, triacontanol is applied at a rate of about $1 \times 10^{-6}$ to 2 grams per acre and each plant hormone used is applied at the rate of about $1 \times 10^{-5}$ to 4 grams per acre.

6. A method according to claim 5 wherein the carrier is an aqueous solution.

7. A method according to claim 6 wherein the composition is applied in the form of an aqueous foliar spray.

8. A method according to claim 6 wherein the composition is applied to the soil.

9. A method according to claim 6 wherein the composition is applied to plant seeds prior to planting.

10. A method according to claim 6 wherein the carrier is buffered to a pH of between about 7 and 8.

* * * * *